United States Patent [19] [11] 4,374,360
Sepponen [45] Feb. 15, 1983

[54] NMR DIAGNOSIS APPARATUS
[76] Inventor: Raimo E. Sepponen, Pitkänsillanranta 7-9 C 111, 00530 Helsinki 53, Finland
[21] Appl. No.: 154,595
[22] Filed: May 29, 1980
[51] Int. Cl.³ .......................................... G01N 27/00
[52] U.S. Cl. .................................. 324/309; 324/320
[58] Field of Search .............. 324/300, 309, 320, 321, 324/318

[56] References Cited
U.S. PATENT DOCUMENTS
3,287,630 11/1966 Gang .................................. 324/320
4,015,196 3/1977 Moore ................................ 324/309

Primary Examiner—Michael J. Tokar
Attorney, Agent, or Firm—Andrus, Sceales, Starke & Sawall

[57] ABSTRACT

A nuclear magnetic resonance diagnosis apparatus includes first members which generate an inhomogeneous magnetic field within which the object is placed, and second members which includes a member which is rotated mechanically within the field. A mechanical motion of the member continuously modifies the strength of the inhomogeneous magnetic field except for a sampling line on the axis of rotation. The sampling line is located to pass through the sampling point. The field strength on the sampling line is at a constant prescribed intensity. It is advantageous in actual practice to carry out the apparatus of the invention. The first members include a solenoid magnet of a supra-conductor with a central axis coinciding with the sampling line. The second members include a rotatably carried permanent magnet having a central axis of rotation on the central axis of the solenoid magnet. The magnetic field strength of predetermined magnitude or intensity occurs only at one point which is a given distance from the central point of the solenoid on the solenoid's central axis.

9 Claims, 4 Drawing Figures

NMR DIAGNOSIS APPARATUS

BACKGROUND OF THE INVENTION

For decades already the NMR (=Nuclear Magnetic Resonance) principle has been employed as a chemical method of analysis. The procedure is based on the behaviour of certain atoms as if they were tiny magnets. These "magnets" may be controlled like common magnets with the aid of an external magnetic field. If a sample containing such atoms (protons) is placed in a strong external magnetic field, the majority of the magnets constituted by protons will orient themselves parallel to the field. The protons are then at their lowest energy level, and therefore the internal energy of the sample is at its minimum. It is however possible to increase the energy level of the sample by irradiating it with electromagnetic radiation, which excites the protons to a higher energy level. Protons are however unable to take up energy other than in quanta of a given size. The quantum size depends on the external magnetic field:

$$E = V B_o$$

$V$ = constant
$B_o$ = external magnetic field.

To this quantum corresponds an electromagnetic radiation having the frequency $$f = E/h$$

$h$ = constant
$f$ = frequency
$E$ = quantum energy.

In other words, the exciting frequency is directly proportional to the strength of the magnetic field $$f = k B_o$$

$k = v/h$ = constant

Likewise, when returning to a lower energy level, protons emit electromagnetic radiation with a frequency directly proportional to the external magnetic field. Therefore if the sample is placed as it is in a magnetic field of which the strength varies in a known manner dependent on location, one is thereby enabled to excite certain protons or to receive the signals emitted by protons located at a given spot (in a given field strength). Hereon are based various NMR image-forming methods by the aid of which the proton density in various parts of the body is mapped.

The signal obtained from the sample also contains information on the tissue from which the signal originates. An NMR signal S departing from a biological tissue has the form $$S = \rho T_2 / T_1$$

$\rho$ = proton density
$T_2$ = SPIN-SPIN relaxation time
$T_1$ = SPIN-AMBIENCE relaxation time.

$T_1$ contains information on the ambience wherein the protons emitting the signal reside. The frequency of the NMR signal is also dependent on the mode of binding of the proton to the surrounding atoms (so-called Chemical Shift). It is possible with the aid of the Chemical Shift, for instance, to distinguish between unbound inorganic phosphorus and e.g. phosphorus bound to ATP. (ATP=Adenosine triphosphate—the energy stores of the biological cell. As the cell consumes energy, ATP divides into ADP and free phosphorus.)

It is possible, by determining in a tissue the average proportions of bound and free phosphorus, to conclude which is the situation of the cells nutritional supply. It is thus possible to distinguish for instance between infarcted tissue and healthy tissue in the cardiac muscle, or to monitor the reactions of the organism to a renal transplant.

But NMR mapping apparatus known in the art, whereof types have been developed e.g. in Great Britain and in the U.S.A., is expensive and implies prolonged image-forming times (several tens of minutes). It is possible in such procedures to produce cross sectional images of the human body just like in computer x-ray tomography. Clinically, however, image-forming is not indispensable; it would suffice if one were able to study a given part of the body, for example the liver, kidney, etc. With this state of prior art as starting point, the object of the invention is an NMR diagnosis apparatus comprising members for producing a magnetic field covering the object of study, a transmitter for transmitting high-frequency electromagnetic radiation to strike the object of study, a receiver for reception of the so-called NMR signal emitted by the irradiated object, and means for processing and analysing the signal.

An apparatus of this kind is known e.g. through the U.S. Pat. No. 3,789,832. One attempts with this apparatus of prior art, by means of NMR image-forming, to achieve a mapping of the whole body in order to detect a malignant growth on the basis of the differences between malignant cancer growth and normal tissue, which could be seen in the changes of the relaxation times in the NMR signal. In malignant tissues, the above-mentioned relaxation time $T_1$ was substantially shorter than in equivalent normal tissues.

The most expensive components in NMR equipment are the blocks forming the magnetic field. The requisite field strength is between 0.1 and 0.2 T, which is equivalent to a proton frequency of 4 to 8 MHz. It is therefore possible most efficiently to reduce the price of the apparatus by simplifying the magnetic field forming.

SUMMARY OF THE INVENTION

The object of the invention is to provide an NMR diagnosis apparatus which instead of image-forming operates on a "sampling" principle, thereby rendering possible substantially simpler and less expensive members than heretofore for the forming of the magnetic field. By such apparatus, the clinician is enabled to study any desired part of tissue and to monitor the changes taking place in this tissue.

In order to attain this end, the NMR diagnosis apparatus of the invention is characterized in that the members for producing the magnetic field comprise first members which generate an inhomogeneous magnetic field, and second members which with the aid of mechanical motion continuously modify the strength of said inhomogeneous magnetic field except for the sampling line passing through the sampling point, where the constant field strength of prescribed intensity, meant to be used towards NMR diagnosis, is present in a small, locally confined region which has been arranged so that it can be accurely pinpointed.

NMR apparatus of this kind commands a price which is only a fraction of that of NMR image-forming equipment for total body mapping because, for instance, the extensive homogeneous magnetic field required in total body image-forming is not required. Also unnecessary are the complex magnetic field gradient arrangements. Moreover, the signal processing is considerably simplified and, among other things, the requisite computer memory capacity is decisively reduced.

It is advantageous in actual practice to carry out the apparatus of the invention so that the first members comprise a solenoid magnet carried out with a supra-conductor, and its central axis coinciding with said sampling line, and that the second members provided for generating a continuously changing field intensity comprise a rotatably carried permanent magnet having for its central axis of rotation, the central axis of the solenoid magnet. In this way it has been ensured by simple apparatus dispositions that a magnetic field strength of predetermined magnitude occurs at one point only, which is locally confined and of which the location is accurately known. This point is at a given distance from the central point of the solenoid on the solenoid's central axis, with which the axis of rotation of the permanent magnet coincides.

BRIEF DESCRIPTION OF DRAWINGS

The invention is described in the following with reference to the attached drawings, wherein.

DESCRIPTION OF ILLUSTRATED EMBODIMENT

Figure 1:
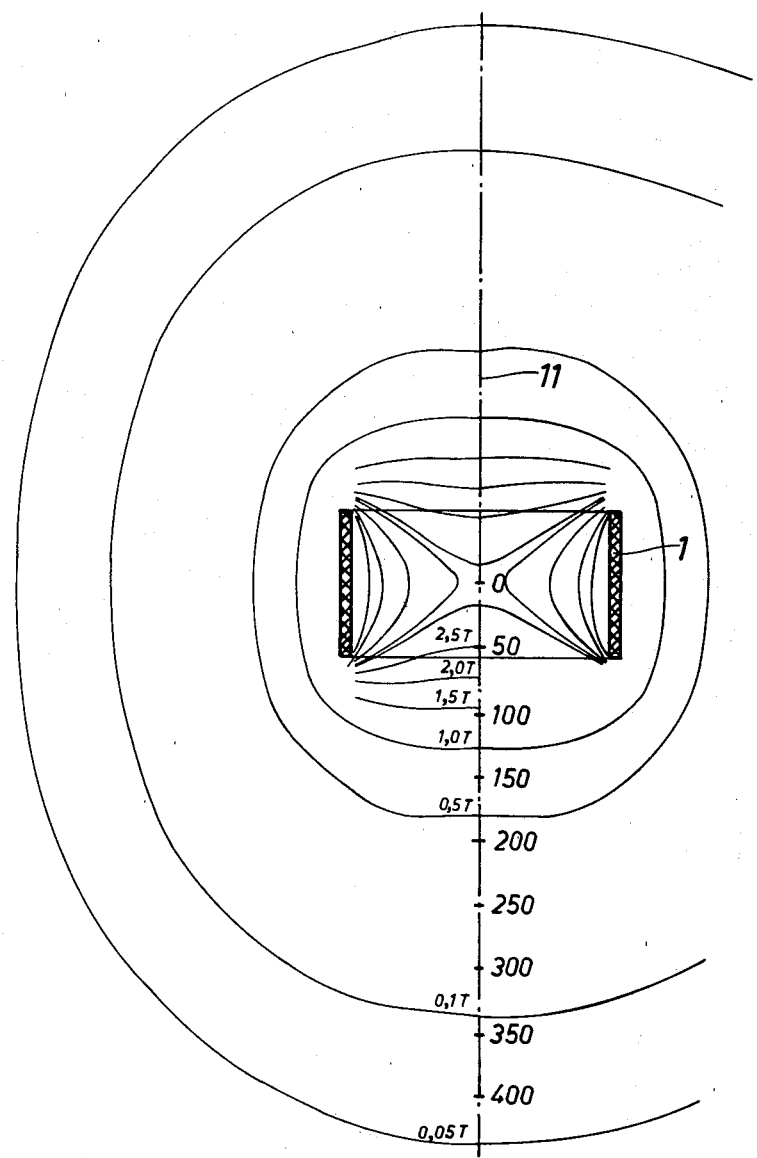
FIG. 1 presents the field of a simple solenoid magnet carried out with a supra-conductor.
Figure 2A:
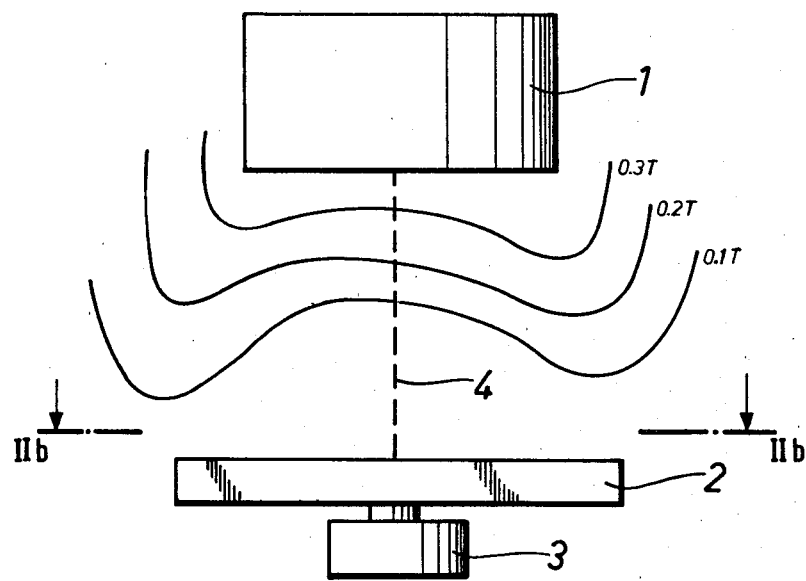
FIG. 2a and FIG. 2b the disposal according to the invention of the magnets in the apparatus for generating the magnetic field that is to be used.
Figure 2B:
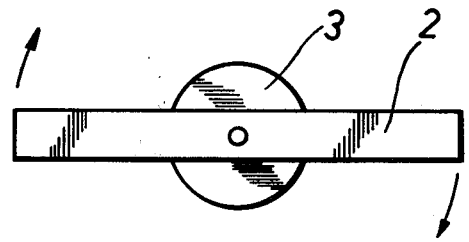
Figure 3:
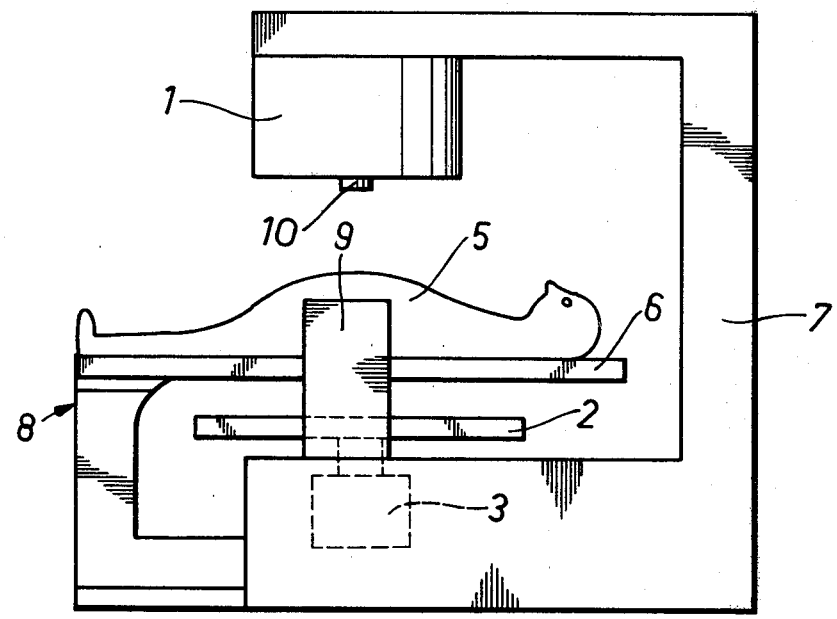
FIG. 3 presents schematically, in elevational view, the diagnosis apparatus of the invention.

As can be seen in FIG. 1, the required field strength, e.g. 0.1 T, is obtained at a distance about 35 cm from the central point of the solenoid 1 on its central axis 11. A magnet of this type is exceedingly simple to manufacture, but its field pattern is such that it presents the said 0.1 T field over extensive regions. For this reason, this field is not usable towards NMR analysis since it is not known from which point with the respective field strength the NMR signal is received. For this reason, in the apparatus of the invention this field is modified so that one given point only meets the requirements imposed on generation of the NMR signal. A simple and inexpensive solution to this problem has been found by using a kind of "field mill" which by means of mechanical motion creates disturbances which scramble the field outside the desired region. In FIG. 3 is shown a simple structural design of such a "field mill". Under the solenoid magnet 1 has been placed a ferromagnetic rod 2 rotated by means of a motor 3, and which as it rotates alters the field pattern locally and cyclically everywhere except on the line 4 connecting the central points of the solenoid 1 and the rod 2. Thus, the field is only stable on this line and this line only satisfies the conditions for generation of the NMR signal. Along the line 4, a stable field gradient is active, whereby the point of examination on the line 4 can be selected by the aid of the frequency of the exciting signal. It is thus understood that with the aid of the magnet disposition as taught by the invention, a sampling line 4 can be formed on which any desired point may be studied.

A diagnostic apparatus based on the foregoing is shown in FIG. 3. In the apparatus, the magnet 1 establishing the field has been mounted on the frame 7, which in its lower part carries the rotor 2 of the field mill and the rotation motor 3 therefor. The patient who is to be examined, 5, lies upon the displaceable table 6 suspended by means of a set of bearings 8. Also affixed to the frame 7 are the transmitter and receiver coils 9. Further attached to the magnet is a light source 10, which produces a light beam along the line connecting the magnet 1 and the rod 2. This light beam enables the region under examination in the patient to be localised.

As was observed at the outset, substantial advantages are gained by this apparatus over NMR image-forming apparatus of prior art in which electromagnetically generated gradients are used for fixing the point of examination. These advantages include the following:

(a) Simple design of the magnet required to form the field;

(b) Selectivity of the field is achieved by a simple and inexpensive piece of apparatus, such as a rod of ferromagnetic material, in contrast to the earlier need of expensive and complex gradient coils;

(c) No attempt is made to form an image of the object of study, instead of which an NMR analysis is made of the desired body part.

It is clearly understood that the invention is not confined to the embodiment example presented in the drawing and that the details of the apparatus design may vary within the scope of the claims following hereinbelow. For instance, other structures may be used as well instead of the ferrite rod for modifying the field around the object region. The field mill may be symmetrically mounted with reference to the main magnet, on its side or above it.

In addition to the practical applications mentioned, the apparatus of the invention is particularly appropriate for detecting and examining local blood coagulations since when blood coagulates there ensures a substantial change in the ratio $T_1/T_2$ of said relaxation times, compared with the equivalent ratio of uncoagulated blood and surrounding tissues. Since in the apparatus of the invention the location of a constant magnetic field intensity of predetermined magnitude is exactly localisable, even relatively minor coagulated blood pockets can be rapidly detected.

I claim:

1. Nuclear magnetic resonance diagnosis apparatus for creating a magnetic field at the object of examination and having a transmitter for transmitting a high-frequency electro-magnetic radiation to the object under examination and a receiver for reception of the NMR signal emitted by the object irradiated in the magnetic field and transmission of said signal to means for processing and analyzing the signal, comprising first and second means for producing the magnetic field, said first means including a magnetic field generating means to produce an inhomogeneous magnetic field, and said second means including a mechanically movable member located in said magnetic field and a power means to move said member relative to said first member continuously, said movable member being constructed and arranged to modify the strength of said inhomogeneous magnetic field except for a sampling line (4) defining a concentrated elongated volume extending through the object and passing through a sampling point, and extending through said field whereby a constant field strength of a given intensity operable in NMR diagnosis is thereby created within a small, locally circumscribed region, which is accurately pinpointable.

2. The apparatus according to claim 1, wherein the first means includes a solenoid magnet (1) having a supra-conductor, and having a central axis (11) coinciding with said sampling line (4), and said movable member for causing a continuously changing field strength includes a rotatably member mounted with an axis of rotation coincident with and which has the said sampling line (4) for its axis of rotation, said movable member being formed of a ferromagnetic material.

3. Apparatus according to claim 2, characterized in that the member (2) of ferromagnetic material has the shape of an elongated rod of which the axis of rotation is perpendicular to its longitudinal axis.

4. Apparatus according to claim 1, including a table to support said object and said table (6) and the means for creating said magnetic field are movable with reference to each other.

5. Apparatus according to claim 4, wherein the apparatus includes a supporting frame, said table (6) is displaceably mounted in the frame (7) of the apparatus for movement relative to said means.

6. Apparatus according to claim 4 or 5, wherein a transmitter support means for said transmitter and a receiver support means for said receiver coil (9) are fixedly attached to the frame (7) of the apparatus to immovably locate the transmitter and receiver with reference to the means (1,2) provided for creating the magnetic field.

7. Apparatus according to claim 2 including a patient table and wherein said solenoid magnet (1) and said movable member (2) are located on opposite sides of the table (6).

8. Apparatus according to claim 1 wherein a light source is fixedly mounted with reference to the means producing the magnetic field, said light source (10) aiding the examination the course of the sampling line (4) in the patient can be located.

9. Apparatus according to claim 1 including means to detect local blood coagulations.

* * * * *